United States Patent [19]
Nakajima et al.

[11] Patent Number: 5,653,754
[45] Date of Patent: Aug. 5, 1997

[54] DEFORMABLE INTRAOCULAR LENS

[75] Inventors: Toshiyuki Nakajima, Tokyo; Toshikazu Kikuchi, Hachioji, both of Japan

[73] Assignee: Canon Staar Co., Inc., Tokyo, Japan

[21] Appl. No.: 578,912

[22] Filed: Dec. 27, 1995

Related U.S. Application Data

[62] Division of Ser. No. 271,834, Jul. 7, 1994, Pat. No. 5,578,078.

[30] Foreign Application Priority Data

Jul. 15, 1993 [JP] Japan ................................. 5-175330

[51] Int. Cl.⁶ ......................................................... A61F 2/16
[52] U.S. Cl. ............................................................... 623/6
[58] Field of Search ................................................... 623/6

[56] References Cited

U.S. PATENT DOCUMENTS

| | | | |
|---|---|---|---|
| 4,242,761 | 1/1981 | Chase et al. | 623/6 |
| 4,737,322 | 4/1988 | Bruns et al. | 623/6 X |
| 4,786,445 | 11/1988 | Portnoy et al. | 623/6 X |
| 4,888,013 | 12/1989 | Ting et al. | 623/6 |
| 4,894,062 | 1/1990 | Christ et al. | 623/6 |
| 5,141,507 | 8/1992 | Parekh | 623/6 |
| 5,266,241 | 11/1993 | Parekh | 623/6 X |
| 5,306,297 | 4/1994 | Rheinish et al. | 623/6 |
| 5,571,177 | 11/1996 | Deacon et al. | 623/6 |

FOREIGN PATENT DOCUMENTS

| | | |
|---|---|---|
| 558748 | 2/1982 | Japan. |
| 583253 | 8/1992 | Japan. |
| 5103803 | 4/1993 | Japan. |
| 5103808 | 4/1993 | Japan. |
| 5103809 | 4/1993 | Japan. |

*Primary Examiner*—Mary Beth Jones
*Attorney, Agent, or Firm*—Ladas & Parry

[57] ABSTRACT

A deformable intraocular lens which does not deviate within the eye and is free from strains or deformation even when the tails of the supports are deformed by external force such as compression.

The lens according to the invention has a deformable optical part which is made of an elastic material, and a plurality of supports which are made of a material different from that of the optical part and which are bonded to the optical part, each of the supports having, in a serial integration, a flexible tail, a rigid base which cuts off the transmission of stress generated by the deformation of the tail to the optical part, and an anchor which binds the support to the optical part, wherein the transitional part of the tail and the base is disposed outside the optical part. With this structure, even when the tails of the supports are deformed by external force, the tails themselves absorb the deformation stress and the rigid bases cut off transmission of the stress to the optical part.

13 Claims, 2 Drawing Sheets

DEFORMABLE INTRAOCULAR LENS

This is a divisional of application Ser. No. 08/271,834 filed Jul. 7, 1994, now U.S. Pat. No. 5,578,078

BACKGROUND OF THE INVENTION

1. Field of the Invention

The present invention relates to a deformable intraocular lens which is inserted into the eye in place of the natural lens when the latter is physically extracted because of cataracts.

2. Description of the Related Art

It is generally accepted that when a cataract-impaired lens is surgically extracted, smaller incisions in the eyeball cause less chance of postoperative astigmatism.

Accordingly, a technique called KPE (Kelman's pharmacoemulsification; suction of lens substance crushed by ultrasonic emulsification) using an ultrasonic emulsification/suction apparatus has been developed. With this apparatus, an opaqued lens is crushed and emulsified by ultrasonication, and then sucked for removal. This technique permits an operation in which lenses are extracted through a small incision of approximately 4 mm, as compared to larger incisions of about 10 mm according to the conventional ECCE operation technique (extracapsular cataract extraction).

In connection with the technique which made small incisions possible as mentioned above, intraocular lenses which can be inserted through a small incision have been developed. Conventional intraocular lenses have an optical part made of a hard material such as glass or plastic, and therefore, the incisions prepared at the time of transplant are greater than the diameter of the optical part which are in most cases 6.5 mm or more. Accordingly, even though a lens is extracted through a small incision according to the KPE technique, it is necessary that the incision be enlarged when a hard intraocular lens is inserted.

To solve this problem, Japanese Patent Application No. S58-18005 (Japanese Patent Application Laid-open (kokai) No. 146346/1983 Japanese Patent Publication No. H5-58748) discloses a deformable intraocular lens which can be inserted through a small incision made in an eyeball. As shown in FIG. 4 (Prior Art), such an intraocular lens is composed of an optical part 3 made of an elastic material and having predetermined memory characteristics and a plurality of supports 4 which hold the optical part within the eye and which are made of a different material from the optical part 3. Anchors of the supports 4 are embedded in the optical part 3 for bonding the supports to the optical part.

The optical part 3 can be deformed by rolling, bending, extending or folding to reduce its size. Therefore, an intraocular lens having such an optical part can be inserted through a small incision prepared in the eyeball with a newly developed inserting device which can deform the optical part. With this inserting device, the intraocular lens can be inserted through a small incision of about 4 mm in diameter, and can be restored to its original larger shape within the eye, based on the memory characteristics of the optical part 3. Thus, neither the size of the intraocular lens itself nor the method of inserting the lens requires the creation of a large incision.

The above-described deformable intraocular lens according to the prior art involves a drawback that the optical part 3 tends to deviate within the eye. When the supports 4 support the deformable optical part 3 within the eye, they are deformed by external force such as compression force, tensile force, etc., and stress such as compression stress generated in the supports 4 are transmitted to the optical part 3 to generate strains or deformation in the areas 3a of the concave lens shown by the chain lines in FIG. 4, which areas are close to the positions at which the anchors 4a of the supports 4 are embedded.

SUMMARY OF THE INVENTION

The present invention addresses the above-mentioned problems by providing a deformable intraocular lens which does not cause deviation or decentralization of the optical part when the tails of the supports are deformed by external force.

According to the present invention, there is provided a deformable intraocular lens comprising a deformable optical part which is made of an elastic material and which has predetermined memory characteristics, and a plurality of supports which are made of a material different from that of the optical part and which are bonded to the optical part, each of the supports having, in a serial integration, a flexible tail, a rigid base which cuts off the transmission of stress generated by the deformation of the tail to the optical part, and an anchor which binds the support to the optical part, wherein the transitional part of the tail and the base is disposed at a position outside of the optical part.

DESCRIPTION OF THE PREFERRED EMBODIMENTS

A first embodiment of the present invention will be described while referring to FIGS. 1 and 2.

Figure 1:
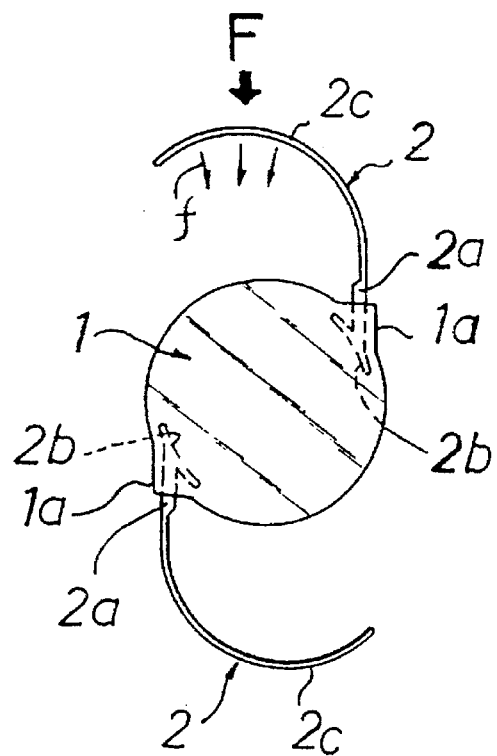
FIG. 1 is a plan view showing a deformable intraocular lens according to a first embodiment of the present invention.
Figure 2:
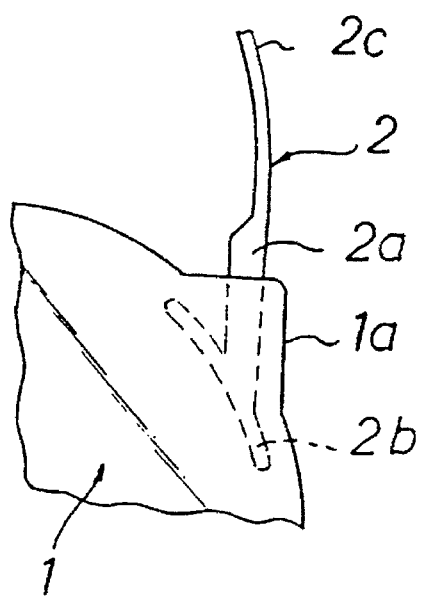
FIG. 2 is an enlarged plan view showing a portion of the deformable intraocular lens of FIG. 1.

In FIGS. 1 and 2, numeral 1 denotes an optical part made of a molded deformable elastic material which has predetermined memory characteristics and which has an approximately round front view. The optical part 1 is provided with a pair of reinforcing sections 1a at the right-upper position and the left-lower position in FIG. 1. They protrude from the optical part 1, and form an approximately right angle at each of the protruding corners.

Numeral 2 denotes a support made of a flexible material which is different from the material used for the optical part 1. Each of the supports 2, 2 is composed of a base 2a which is relatively wide and thick, an arcuate anchor 2b which is integrally formed with the base 2a, and a tail 2c which has a small width and which is integrally connected to the base 2a.

Two supports 2, 2 are provided to form the optical part 1. The substantial part of the base 2a and the anchor 2b are embedded in and bonded to the reinforcing section 1a and the peripheral portion of the optical part 1 at a slightly inner position of the protruding reinforcing section 1a, respectively. The outer periphery of the base 2a is extended in parallel to one side of the reinforcing section 1a as shown in FIG. 1, and one end of the base 2a is slightly protruded outside of the other side of the reinforcing section 1a.

The tail 2c of the support 2 has a spring function of a certain spring force which permits easy deformation of the tail by external force. The portion remote to the base 2a is bent to form a bulged arc as shown in FIG. 1. The ends of the tails 2c are symmetrically disposed with regard to the center of the optical part 1.

The optical part 1 is made of a transparent elastic material such as a polyurethane elastomer, a silicone elastomer, a hydrogel polymer, a collagen compound, etc. The support 2 is made of a flexible synthetic resin such as polyimide.

The deformable intraocular lens of the above described first embodiment is transplanted in the eye with a suitable device such as an inserting device similar to that shown in Japanese Patent Application No. H3-142067. (Japanese Patent Application Laid-open (kokai) No. H5-103803, by inserting it in place of the natural lens which has been extracted through a small incision of about 4 mm, and allowing it to restore to the original shape before it is deformed according to the memory characteristics of the optical part 1.

In the intraocular lens of the first embodiment, the anchor 2b and the substantial part of the base 2a of the support 2 are embedded in the optical part 1, and the thin and flexible tail 2c provided in the support 2 is connected to the wide and rigid base 2a, with the connection part being disposed outside the optical part 1. Therefore, even when compression stress shown by arrow F in FIG. 1 is imposed on the tail 2c, the compression stress is absorbed by the tail 2c as it bends in the direction shown by arrows f. The compression stress imposed on the tail 2c, therefore, is not transmitted to the rigid base 2a, and the deformable optical part 1 is free from strains or deformation. Accordingly, even when compression stress is imposed on the tail 2c, the optical part 1 does not deviate.

Although the above description, for convenience, refers to the situation where compression stress is imposed on the tail 2c of the support 2, the same effect can be obtained when the tails 2c undergo external force such as tensile, etc. That is, the stress is not transmitted to the bases 2a. Therefore, deviation of the optical part 1, or strains or deformation in the optical part 1 does not occur.

A second embodiment of the present invention will be described while referring to FIG. 3.

Figure 3:
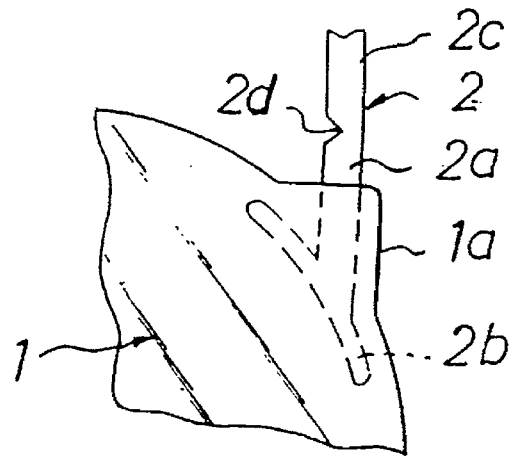
FIG. 3 is an enlarged plan view showing a portion of the deformable intraocular lens according to a second embodiment of the invention.
Figure 4:
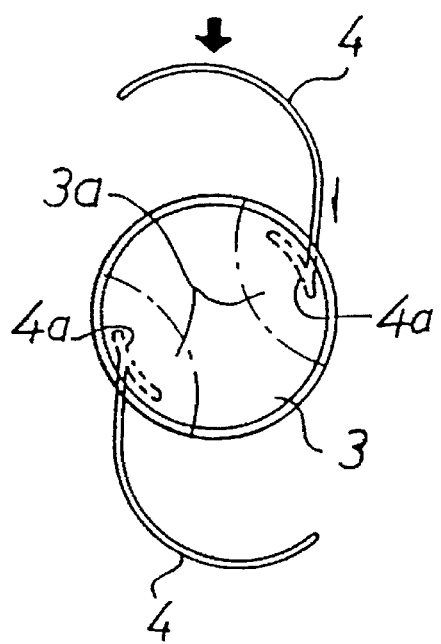
FIG. 4 (Prior Art) is an enlarged plan view showing a portion of a deformable intraocular lens according to the prior art.

In FIG. 3, numeral 1 denotes an optical part, and numeral 2 denotes a support. The support 2 has a notch 2d at the position at which the base 2a is connected to the tail 2c, and the V-shape opening faces the inner area which is embraced by the tail 2c. In this embodiment, the width of the tail 2c is equal to that of the base 2a. The structure other than described is the same as that mentioned in the first embodiment. The same numbers in FIGS. 1 to 3 indicate the same or the corresponding parts.

The intraocular lens according to the second embodiment of the invention is used, same as the lens in the first embodiment, by inserting it in the eye with an inserting device in place of a natural lens which has been extracted from a small incision. When the tail 2c undergoes external force such as compression or tensile force, it bends to absorb the stress due to the presence of the notch 2d provided at the transition position between the tail 2c and the base 2a of the support 2. Accordingly, neither deviation of the optical part 1, nor strains or deformation in the optical part 1 occur as in the first embodiment.

In the present invention, the tail of the support may be formed thinner than the base 2a as in the first embodiment, and the transition position between them may be provided with a notch as in the second embodiment.

As described above, since the deformable intraocular lens according to the present invention has a structure which comprises an optical part which is made of an elastic material having predetermined memory characteristics and a plurality of supports which are made of a material different from that of the optical part and which are bonded to the optical part, each of the supports having, in a serial integration, a flexible tail, a rigid base which cuts off the transmission of stress generated by the deformation of the tail to the optical part, and an anchor which binds the support to the optical part, wherein the transitional part of the tail and the base is disposed outside the optical part, the intraocular lens of the present invention has the following advantage.

That is, the deformable intraocular lens according to the present invention does not cause deviation of the optical part and is free from strains or deformation of the optical part, because the stress is not transmitted to the optical part due to such a structure that the stress generated in the supports as a result of external force such as compression, tensile, etc., imposed on the supports when the supports hold the deformable optical part, is absorbed by the flexible tails of the supports and prevents the mentioned stress from being transmitted to the rigid bases. Since the tail and the base of each support are connected with each other outside of the optional part, the stress is not transmitted to the optical part. Therefore, the optical part does neither deviate within the eye nor generate strains or deformation.

What is claimed is:

1. A deformable intraocular lens having predetermined memory characteristics, the lens comprising:
    (a) an optical part, the optical part having a central portion and a peripheral portion; and
    (b) a plurality of supports, each support comprising a tail, a rigid base, and an anchor, the base having a proximal end and a distal end, the distal end being farther than the proximal end from the central portion of the optical part, the distal end being integrally connected to the tail at a connection part, the proximal end being integrally disposed inside the peripheral portion of the anchor, the anchor being connected to the optical part, the distal end of the base protruding from the peripheral portion of the optical part, the connection part being disposed outside of the peripheral portion of the optical part, the connection part having a notch.

2. A deformable intraocular lens as claimed in claim 1, wherein the base and the tail are equally wide.

3. A deformable intraocular lens as claimed in claim 1, wherein the tail curves in a direction, and the notch opens toward the direction.

4. A deformable intraocular lens as claimed in claim 2, wherein the tail curves in a direction, and the notch opens toward the direction.

5. A deformable intraocular lens as claimed in claim 1, wherein the optical part further has a plurality of reinforcing sections; each support is associated with a corresponding reinforcing section; each reinforcing section protrudes from the peripheral portion of the optical part; and the distal end of the base protrudes from the reinforcing section.

6. A deformable intraocular lens as claimed in claim 2, wherein the optical part further has a plurality of reinforcing sections; each support is associated with a corresponding reinforcing section; each reinforcing section protrudes from the peripheral portion of the optical part; and the distal end of the base protrudes from the reinforcing section.

7. A deformable intraocular lens as claimed in claim 3, wherein the optical part further has a plurality of reinforcing sections; each support is associated with a corresponding reinforcing section; each reinforcing section protrudes from the peripheral portion of the optical part; and the distal end of the base protrudes from the reinforcing section.

8. A deformable intraocular lens as claimed in claim 4, wherein the optical part further has a plurality of reinforcing sections; each support is associated with a corresponding reinforcing section; each reinforcing section protrudes from the peripheral portion of the optical part; and the distal end of the base protrudes from the reinforcing section.

9. A deformable intraocular lens as claimed in claim 5, wherein the reinforcing section protrudes to form an angle of approximately 90 degrees.

10. A deformable intraocular lens as claimed in claim 7, wherein the reinforcing section protrudes to form an angle of approximately 90 degrees.

11. A deformable intraocular lens as claimed in claim 1, wherein the optical part is made of an elastic material; and each support is made of a material different than the elastic material.

12. A deformable intraocular lens as claimed in claim 5, wherein the optical part is made of an elastic material; and each support is made of a material different than the elastic material.

13. A deformable intraocular lens as claimed in claim 1, wherein each support is made of a flexible synthetic resin.

* * * * *